(12) United States Patent
Buchwald et al.

(10) Patent No.: US 8,767,201 B2
(45) Date of Patent: Jul. 1, 2014

(54) BOTTLE SEAM AND EMBOSSING ALIGNMENT (75) Inventors: Carsten Buchwald, Bad Breisig (DE); Wolfgang Schorn, Hönningen (DE)

(73) Assignee: KHS GmbH, Dortmund (DE)

( * ) Notice: Subject to any disclaimer, the term of this patent is extended or adjusted under 35 U.S.C. 154(b) by 78 days.

(21) Appl. No.: 13/059,272

(22) PCT Filed: Oct. 28, 2009

(86) PCT No.: PCT/EP2009/007705
§ 371 (c)(1),
(2), (4) Date: Mar. 10, 2011

(87) PCT Pub. No.: WO2010/049137
PCT Pub. Date: May 6, 2010

(65) Prior Publication Data
US 2011/0181874 A1    Jul. 28, 2011

(30) Foreign Application Priority Data
Oct. 30, 2008  (DE) .......................... 10 2008 053 876

(51) Int. Cl.
*G01N 21/00* (2006.01)
(52) U.S. Cl.
USPC ..................................... 356/239.4; 356/239.7
(58) Field of Classification Search
USPC ................... 356/71, 256, 239.4, 239.1, 239.5, 356/239.7, 239.8, 240.1; 250/223 B; 382/141, 142; 362/11; 348/127, 125
See application file for complete search history.

(56) References Cited

U.S. PATENT DOCUMENTS 3,814,521 A    6/1974  Free
2009/0290781 A1  11/2009 Yannick et al.

FOREIGN PATENT DOCUMENTS

| DE | 19741384 | 3/1999 | |
|----|----------|--------|---|
| DE | 29907762 | 10/1999 | |
| DE | 102004040164 | 3/2006 | |
| DE | WO 2007/095928 A2 * | 8/2007 | ................. 356/239.4 |
| DE | 102006008840 | 9/2007 | |
| DE | 102008018096 | 11/2009 | |
| EP | 1628241 | 2/2006 | |
| JP | 08-015163 | 1/2008 | |
| JP | 10-068612 | 3/2010 | |
| WO | 03/042673 | 5/2003 | |

* cited by examiner

*Primary Examiner* — Tri T Ton
(74) *Attorney, Agent, or Firm* — Occhiuti & Rohlicek LLP

(57) ABSTRACT

A detecting system for detecting containers that exhibit features located on a container wall thereof includes a lighting unit having a plurality of light sources. The lighting unit is configured to project spaced-apart strip-shaped light beams onto a region of the container wall. The system also includes an optical arrangement having at least one camera.

17 Claims, 5 Drawing Sheets

Fig. 7

BOTTLE SEAM AND EMBOSSING ALIGNMENT

CROSS-REFERENCE TO RELATED APPLICATIONS

This application is the National Stage of International Application No. PCT/EP2009/007705, filed on Oct. 28, 2009, which claims the priority of German Patent Application No. 10 2008 053 876.0, filed on Oct. 30, 2008. The contents of both applications are hereby incorporated by reference in their entirety.

FIELD OF DISCLOSURE

The invention relates to a detecting system for detecting bottles or similar containers that exhibit features located on a container wall, wherein the detecting system includes a lighting unit and an optical arrangement with at least one camera.

BACKGROUND

These types of containers can be used in the manner of bottles or the like for liquids, for example for beverages. The containers can be produced from a transparent, translucent or opaque material, for example from glass or a translucent plastics material, e.g. PET, and exhibit a glossy surface. The most varied types of fill media can be filled in the containers, it also being possible for the containers to be in different colours. The containers are supplied, for example, to a labelling machine, in which a label is to be arranged in a predetermined and repeatable position always identically oriented in relation to external positional or development features or embossings on the outside of the container. The label, however, not only has to be aligned correctly in relation to the embossings or other features, but must also be arranged on the container in as crease-free a manner as possible or without any elevations and/or indentations. However, containers can have two vertically extending bottle seams that are arranged directly opposite one another or can also have only one bottle seam. In this respect, to all intents and purposes, it is desirable for the label not to be applied onto one of the bottle seams or on the bottle seam or container seam, as this disturbs the visual appearance of the label or of the container as the label can have a crease (elevation/indentation) in the region of the bottle seam such that the impression is given that the label has been carelessly applied to the container and this can result in end consumers avoiding the product.

SUMMARY

Consequently, it is the object of the invention to provide a detecting system of the aforementioned type which recognizes features on the container using simple means, such that the label cannot be applied onto a bottle seam and/or can be arranged correctly aligned in relation to embossings on the container.

The object is achieved according to the invention through a detecting system with the features of claim 1, the lighting unit including a plurality of light sources and being realized such that a strip-shaped light beam is projected from the respective light source onto a container wall region, the light beams projected in a strip-shaped manner onto the container wall region in each case being spaced apart.

In a favourable design, the lighting unit is realized such that vertically aligned light beams are projected onto the container wall region.

In a first development of the lighting unit, it is provided in an advantageous manner that said lighting unit has a carrier element with a light surface that is oriented towards the container. In a preferred design at least one conductor path can be arranged on the light surface, the light sources being arranged spaced apart, oriented vertically on said conductor path. The conductor path is preferably flexible, that-is-to-say bendable and includes vertically arranged photo strips for the light sources such that a strip-shaped pattern is projected onto the container wall region. The light sources can be realized, for example, as LED light sources. Naturally the light sources can also be realized as infrared light sources. In a preferred manner, the light sources are pulsed, the optical arrangement or the at least one camera being synchronized with the light source.

In an expedient development, the carrier element or the light surface is realized in the manner of a segment of a circle, which includes the container to be inspected or the container to be detected at least in regions, but is at an axial spacing from said container. In a first development, a single conductor path with light sources located thereon can be arranged on the light surface. However, it is also conceivable to arrange several conductor paths, preferably two conductor paths with light sources arranged thereon on the light surface, the conductor paths being arranged in an expedient manner one above the other, and it being possible in an advantageous manner for the individual rows or strips of light sources to be laterally offset one relative to another.

In an expedient development, the optical arrangement has several, preferably three cameras that are arranged in a favourable manner correlating to the strip pattern projected onto the container wall region, such that the entire container wall region irradiated by the light sources can be photographed. In a favourable design, at least a region of approximately 40% of the total circumference of the container can be photographed by the optical arrangement. Naturally, the arrangement is arranged in an expedient manner so as to be vertically offset in relation to the lighting unit.

The detecting unit is preferably associated with a labelling machine that includes a labelling star. In this respect, the carrier element and also the optical arrangement, in the case of the design with the labelling star, are realizable in dependence on the structural conditions of the labelling star. This means that only a certain container wall region is irradiated by the lighting unit and can be photographed by the optical arrangement. Consequently, in terms of the invention it is expedient for the carrier element to be realized, for example, as a curved metal strip such that said metal strip does not engage in the circular path of the container or of the labelling star. Naturally, the carrier element can also be realized from other suitable materials. The conductor path or conductor paths can be secured to the carrier element in a suitable manner so as to be fixed in position, for example they can be bonded by way of their rear side, to name but one type of securement as an example.

In another favourable development it can be provided that the at least one camera, preferably all the cameras have connected upstream an optical lens, preferably developed as a cylindrical lens in order to spread the strip pattern or the vertical line structure projected onto the container wall region in an optical manner over the entire vertical detecting region. The optical lens can also be realized as a Fresnel lens to name but one other suitable example of an optical lens.

Greater optical resolution can be achieved for the detecting system by means of the advantageously provided optical lens, as the line structure spreads out in a considerably finer manner over the entire detecting region of the optical detecting system. This also naturally applies to the case where the two conductor paths are offset or to the rows or strips of light sources arranged thereon.

On account of the special arrangement of the individual light sources (strips or rows), such a targeted vertical strip pattern is projected onto the container body or onto the container wall region. The advantageous arrangement of the light sources generates in the "total reflection" an image of the entire lighting unit or of its light sources in strips or vertically arranged lines. The arrangement of said lines consequently reflects the surface of the container or of the container wall region to be detected. If there are no changes on the container wall or on the container wall region to be detected, such as, for example, a bottle seam, the lines are always aligned identically in their number one relative to another independently of container rotations or container positions. If the bottle seam falls into said line structure, their number and arrangement one relative to another changes. There is a change in the line imaging, for example. Thus, with the invention, it is possible to determine a position of the container seam in an absolutely precise manner advantageously irrespective of container content and container colour. In a favourable manner, two detecting systems can be provided one after the other such that by rotating the container about, for example 90°, it is possible to determine the position of the container seam in a precise manner, also because the detecting system, in particular by way of its carrier element as afore-described in the case of a labelling star, is not to engage in said star. By rotating the container, a further container wall region can be inspected by the following second detecting system. In this case, the important points underlying the invention are that the container stands upright on a rotatable turntable, and can be rotated when being supplied to the detecting system.

In order to avoid reflections of the container caused by the surrounding area having a negative influence on the precision of the detection, the light sources can be realized as infrared light sources, it also being possible to provide a daylight barrier filter.

By means of detecting or determining the position of the container seam using the reflected light method, it is possible to align the container such that a label can be attached at positions at which there is no container seam, thereby avoiding label elevations (creases).

However, the advantageously realized detecting system can be used within the terms of the invention not only for determining the position of the container seam. As the lighting unit is formed from a plurality of individual targeted light sources, these can also be used in an expedient manner for detecting external development features, so-called embossings. In this case, there is no need for an optical lens in front of the respective cameras, the lighting unit being usable as dark field lighting. As previously, a strip-shaped light pattern is projected onto the container in this case. The embossing, just as the bottle seam, also creates a change on the container surface. Via the "total reflection" (imaging), the structure and the form of the embossing is reflected back. These structures can be learnt by the (optical) detecting system as a function of the position of rotation of the container. Advantageously, the detecting system is thus capable of determining a position of the embossing in an absolutely precise manner irrespective of the content and of the container colour. Where a surface is smooth, that-is-to-say a surface without embossing, there are no glossy points on the strip pattern projected onto the container. The surface appears black to the (optical) detecting system. If, contrary to this, the strip pattern projected onto the container falls onto the embossing or onto the elevations, said glossy points are created and are photographed by the optical arrangement or by the cameras as (white) light points. Between the glossy points the smooth container surface appears black so that the entire embossing is detectable by the camera arrangement by means of the glossy points. By means of detecting the embossing, it is possible to align for correction, that-is-to-say to apply the label in an aligned manner in relation to the embossing.

In another favourable development, the carrier element of the lighting unit is realized as a closure plate, two closure plates being provided at a vertical spacing from each other. Light conductors are arranged between the closure plates that are at a vertical spacing from each other, in the preferred development said light conductors being realized as colourless (crystal clear) Plexiglas bars. In a favourable manner a plurality of light conductors is provided lying directly side by side. The light conductors have associated therewith in each case, on their carrier side located opposite the light surface, a light source that is located as close as possible to the carrier side, preferably with no spacing in between. The advantage here is that the light sources can be located in a more flexible manner with reference to an arrangement on a conductor path; for their position is predetermined statically on the printed circuit board by the fixed arrangement of the photo strips. Contrary to this, the light conductors have a planar rear side or carrier side and a light surface that is situated opposite thereto, it being possible to reduce said light surface by machining, for example by milling in a freely selectable radius, such that once again on the light surface side a lighting unit in the shape of a circular segment is formed. Obviously the end faces of the closure plates located on the light surface can also be machined accordingly at the same time. The advantage of this is that the light generator, that-is-to-say the light conductors arranged in rows next to each other no longer have to be curved, but can be correspondingly worked. The curved light surface is thus homogeneously illuminated.

In order to project a strip pattern onto the container surface, it is consequently advantageous to provide the light surface with a mask, which has vertical light outlet openings, that-is-to-say vertical light strips (slots). Naturally different masks with different slot or light patterns can be arranged on the light surface. An arbitrary pattern can be projected onto the container or onto the container wall region in this manner by means of the respective mask. In an expedient design the mask can be realized as a diaphragm element adapted to the curvature of the light surface, in the preferred design the mask can be realized as a diaphragm plate with slots in predeterminable widths and at predeterminable spacings. Naturally the mask can also be a flexible element in which the slots are admitted in order to be able to use the mask irrespective of the radius of the light surface. The mask can be realized as a function of the container diameter, and/or the resolution of the camera. It is naturally also possible to dimension the light conductors such that several masks can be arranged lying one on top of another, the respective slots of the masks lying one on top of another can then at least be laterally offset one from another. It is also conceivable, however, to cascade the lighting unit, that-is-to-say to provide a plurality of lighting units arranged one on top of another, wherein each lighting unit could have a different mask in each case on its light surface. It is also possible to provide a plurality of light conductors arranged one on top of another and side by side between the closure plates.

With this advantageous further development of the lighting unit also, individual light sources, that-is-to-say the light strips emerging in each case from the slots in the mask are projectable as "total reflection" or imaging onto the container, it certainly could be possible here to rule out expenditure on the production of the conductor paths. The masks, producible individually in each case, also achieve a greater flexibility. It has advantageously been found that the lighting unit produced in this manner, without the mask on its light surface, can also be used as direct light-bright field lighting.

In an advantageous development, the light conductors can be realized as square bars and each side face of said square bar is planar, the adjacent light conductors in each case being arranged with their side faces lying side by side with no gaps in between.

BRIEF DESCRIPTION OF THE FIGURES

Further advantageous developments of the invention are disclosed in the sub claims and in the following description of the Figures, in which, in detail:

Identical parts are always provided with the same references in the different Figures which is why, as a rule, they are only described once.

DETAILED DESCRIPTION

Figure 1:
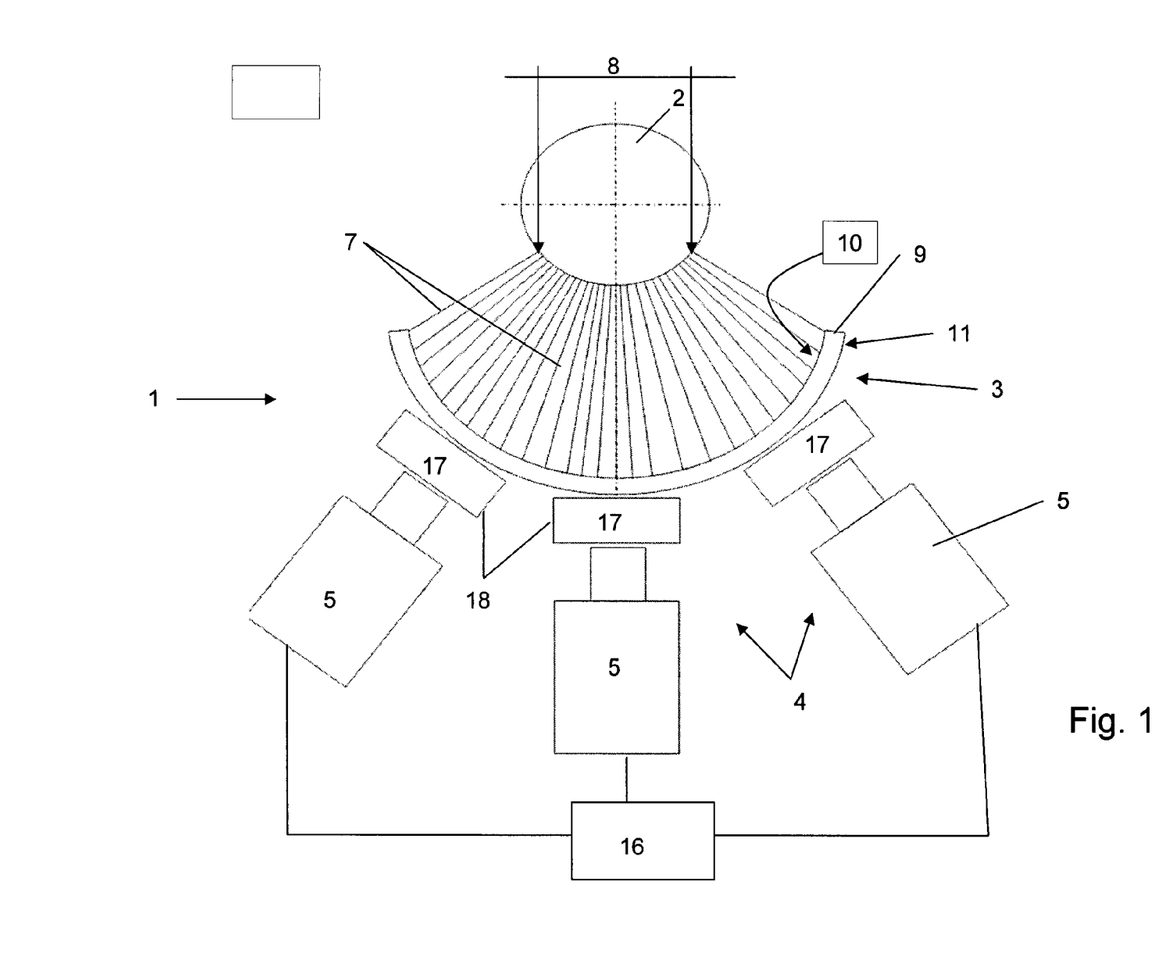
FIG. 1 shows a basic design of a detecting system.

FIG. 1 shows a detecting system 1 for detecting bottles 2 or similar containers. The bottles 2, as an example, can exhibit features located on their container wall such as, for example, bottle seams and/or development features, so-called embossings. The detecting system 1 has a lighting unit 3 and an optical arrangement 4 with at least one camera 5.

The lighting unit 3 has a plurality of light sources 6 (FIG. 2) and is designed such that a strip-shaped light beam 7 is projected by the respective light source 6 onto a container wall region 8, each of the strip-shaped light beams 7 projected onto the container wall region 8 being spaced apart.

The containers or bottles 2 can be produced from a transparent, translucent or opaque material and exhibit a glossy surface. Each bottle 2 can be of different colours and filled with different fill media.

In the case of the exemplary embodiment represented in FIG. 1, the lighting unit 3 has a carrier element 9 with a light surface 10 that is oriented towards the container 2 and a rear side 11 that is oppositely situated thereto. The carrier element 9 is, for example, in the form of a metal strip shaped like a segment of a circle. Other suitable materials can also be used to develop the carrier element 9.

At least one conductor path 12 (FIG. 2) is located on the light surface (10). The conductor path 12 is realized as a flexible conductor path and has vertically arranged photo strips 13, which are arranged side by side spaced apart when viewed in a longitudinal direction of the conductor path 12. The light sources 6 can be arranged on the photo strips 13. The conductor path 12 is connectable to the light surface of the carrier element 9 by way of is rear side.

Figure 2:
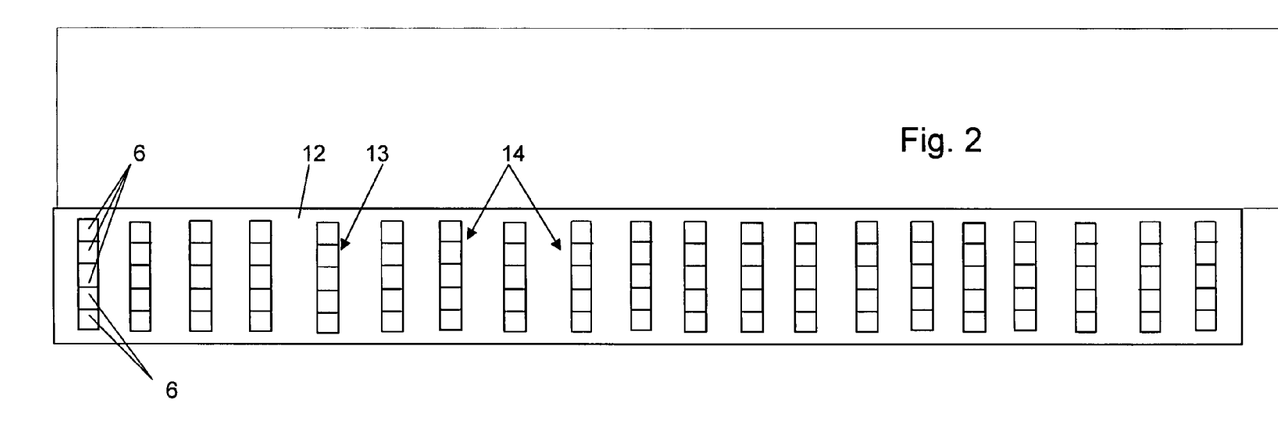
FIG. 2 shows a conductor path in detail.

With the conductor path 12, or with the light sources 6 arranged thereon in vertical rows 14 or lines, a strip-shaped light pattern 15 is projected onto the container wall region 8.

Figure 7:
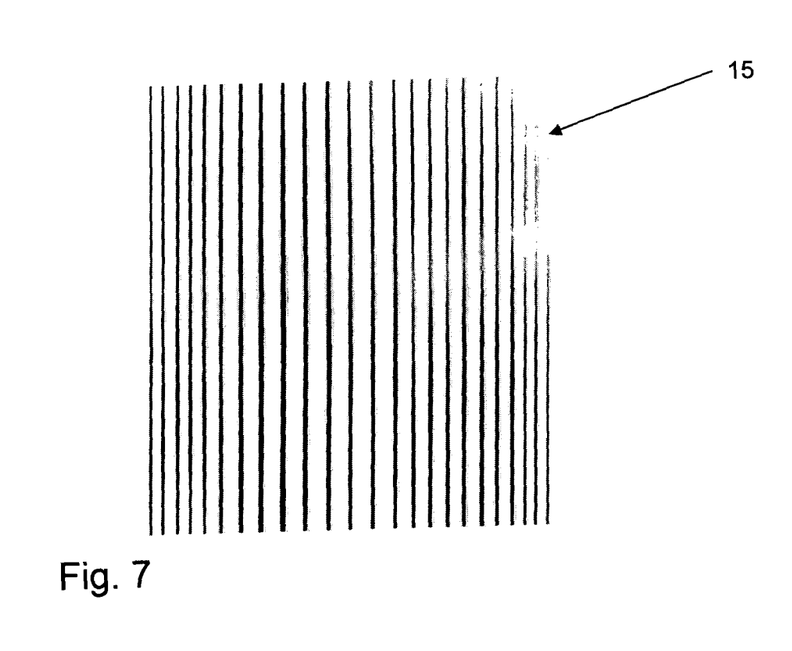
FIG. 7 shows an inverse representation of a light pattern on a container wall and
FIG. 8 shows an inverse representation of an embossing.

A strip-shaped light pattern 15, as an example, which is projected onto a preferably cylindrical container wall region 8, is shown in an inverse representation in FIG. 7. This means that the light beams 7, or the strip-shaped light pattern 15 in an inverse representation is shown black or dark, the non illuminated container wall in the inverse representation appearing white or bright.

Figure 3:
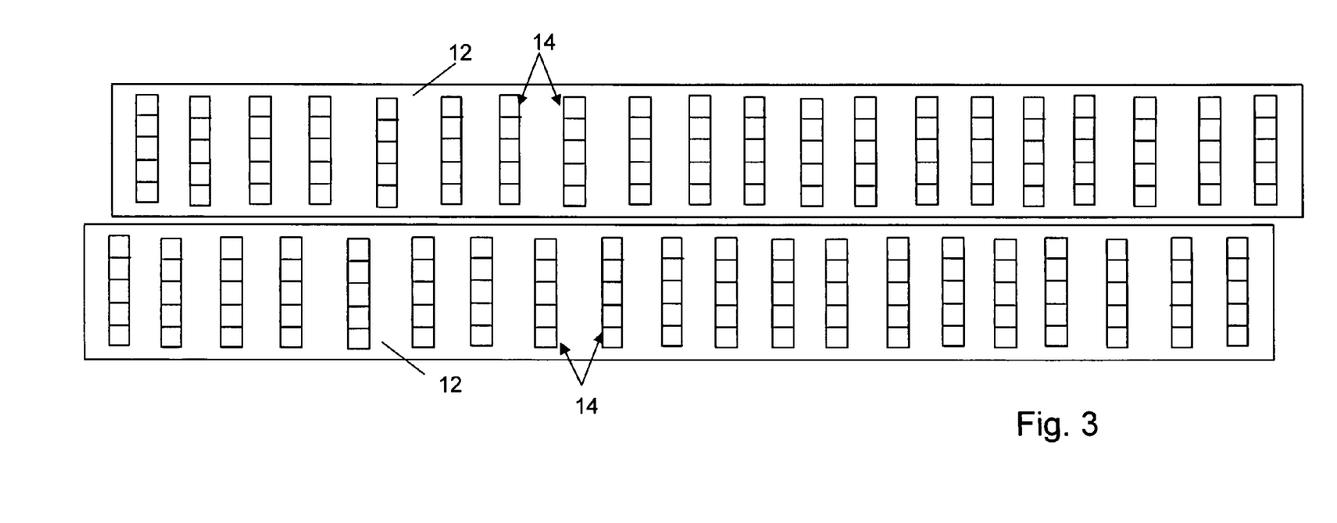
FIG. 3 shows two conductor paths arranged one on top of another with the light strips offset.

However, a plurality of conductor paths 12 can be arranged on the carrier element 9, as is shown as an example in FIG. 3. In this case the conductor paths 12 are arranged with their vertically arranged rows 14 slightly offset laterally one relative to another.

The container 2 according to the exemplary embodiment in FIG. 1 is conveyed past the detecting system 1 in a labelling star of a labelling machine. Consequently, the carrier element 9 is advantageously realized such that said carrier element does not engage in the conveying path (circular path) of the container 2. With the lighting unit 3, such a strip-shaped light pattern 15 can be projected onto a container wall region 8 that corresponds to approximately 40% of the entire circumference of the container 2.

The optical arrangement 4 (FIG. 1) has, as shown as an example, three cameras 5. The cameras 5 are located vertically offset in relation to the lighting unit 3. This means that the optical arrangement 4 can be located above or below the lighting unit 3. The optical arrangement 4 is located such that the container wall region 9 illuminated by the strip-shaped light pattern 15 is photographable. The optical arrangement 4, that-is-to-say each camera 5 is connected to an evaluation and control unit 16, in which the images or image data supplied by the respective camera 5 are evaluated. The processing of the images or image data supplied by the camera 5 is effected for example by comparing them with required data stored in the evaluation and control unit 16. In this respect, the evaluation and control unit 16 can also be identified as an image processing and control unit 16. The evaluation and control unit 16 is, for example, a computer or a computer-supported unit with corresponding inputs for analog or digital data supplied by the respective camera. In addition, the evaluation and control unit 16 has outputs (not shown) that are connected to the individual components (e.g. container aligning means, labelling unit, etc.) of the labelling machine.

Each camera 5 has associated therewith, for example, an optical lens 17. In the exemplary embodiment represented in FIG. 1, the respective optical lens 17 is realized as a cylindrical lens, which is located with its end faces 18 at right angles to the lenses of the respective camera 5. The optical lens 17 can also be realized as a Fresnel lens, to name but one other example.

On account of the special arrangement of the individual light sources 6 (strips or rows 14) such a targeted vertical strip pattern 15 is projected onto the container body or onto the container wall region 8. The advantageous arrangement of the light sources 6 creates in the "total reflection" an image of the entire lighting unit 3 or of its light sources 6 in strips or vertically arranged rows 14. The arrangement of said rows 14 consequently reflects the surface of the container or of the container wall region 8 to be detected. If there are no changes, such as, for example, a bottle seam, located on the container wall or on the container wall region 8 to be detected, the number of rows 14 or the number of the lines in the vertical strip pattern 15 (FIG. 7) are always identically aligned one relative to another irrespective of container rotations or container positions. However, if the bottle seam comes into said line structure (strip-shaped light pattern 15), the number and arrangement of the rows 14 alter in respect to each other. For example, there is a change in the line image. With the invention it is thus possible, advantageously irrespective of container content or container colour, to determine a position of the container seam or the bottle seam in an absolutely precise manner.

In a favourable manner, it is possible to provide two detecting systems following one after the other such that by rotating the container by, for example, 90°, precise determining of the position of the container seam is ensured, also because the detecting system 1, in particular by way of its carrier element 9, as above-described in the case of a labelling star, is not to engage in said star. By rotating the container 2, a further container wall region 8 can be inspected by way of the following, second detecting system. In this case, the important points underlying the invention are that the container stands upright on a rotatable turntable and is able to be rotated when supplied to the detecting system 1.

Figure 8:
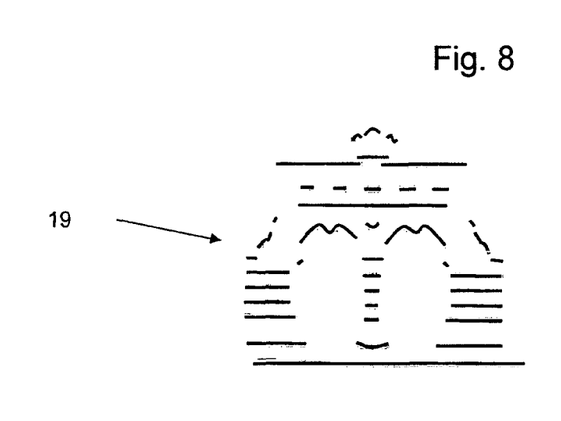

As can be seen in FIG. 8, the detecting system 1 can also be used to recognize external development features, so-called embossings 19 as the lighting unit 3 is formed by a plurality of light sources 6 that are arranged in an individually targeted manner. FIG. 8 is also an inverse representation of the image taken by the cameras 5. In this case, there is no need for an optical lens in front of the respective cameras 5, it being possible to use the lighting unit 3 as dark field lighting. As previously, a strip-shaped light pattern 15 is projected onto the container in this case. The embossing 19 also generates, just as the bottle seam, a change on the container surface. Via the "total reflection" (imaging), the structure and the form of the embossing is reflected again. Said structures can be learnt by the (optical) detecting system 12 as a function of the position of rotation of the container 2. In an advantageous manner, the detecting system 1 is thus capable of determining a position of the embossing 19 in an absolutely precise manner. If the surface is smooth, that-is-to-say a surface without embossing, there are no glossy points in the strip pattern 15 projected onto the container. The surface appears black or dark (inverse to white or bright) to the optical detecting system 1. If, contrary to this, the strip pattern 15 projected onto the container 2 falls onto the embossing 19, or onto the elevations, said glossy points are generated and are photographed by the optical arrangement or by the cameras as (white or bright) light points (inverse to black or dark light points). Between the glossy points the smooth container surface appears black or dark (inverse to white or bright), such that the entire embossing 19 is detectable by the optical arrangement 4 by means of the glossy points. An alignment for correction, that-is-to-say applying the label aligned in relation to the embossing 19 is possible by means of detecting the embossing 19.

Figure 4:
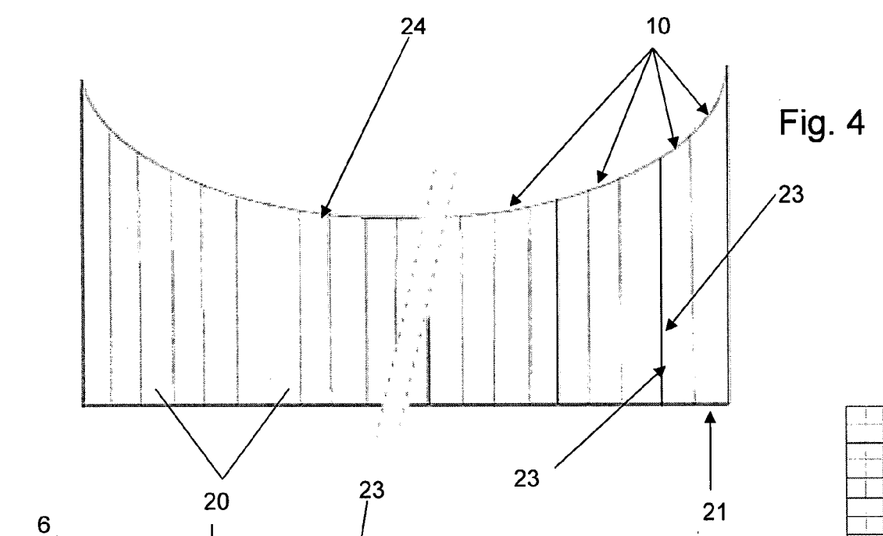
FIG. 4 shows a top view of a lighting unit in an advantageous further development.

In the case of the exemplary embodiment shown in FIG. 4, the lighting unit 3 is formed from a plurality of light conductors 20, which each have a light source 6 on their rear side 21 or carrier side 21. The rear side 21 is located opposite the light surface 10 of the lighting unit 3.

Figure 5:
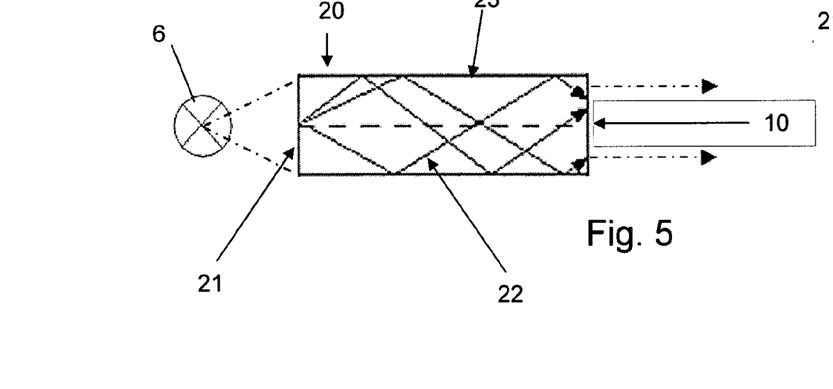
FIG. 5 shows a light coupling into a light conductor of the lighting unit in FIG. 4.

FIG. 5 shows a light conductor in detail. Contrary to the arrangement represented in FIG. 5 of the respective light source in relation to the respective light conductor 20, the light source 6 is preferably at a small spacing from the rear side 21, most preferably at no spacing whatsoever from the rear side 21. The light emitted from the light source 6 is coupled into the light conductor 20 at the rear and emerges from the light conductor 20 on the light surface side. This is shown as an example by means of the beam entry 22.

The respective light conductor 20 is preferably realized as a colourless (crystal clear) Plexiglas bar in the form of a square bar. The light conductors 20 lie side by side with side faces 23 adjacent in each case with no gap between.

The light conductors 20 are held between two closure plates that are vertically spaced apart (not shown).

According to the exemplary embodiment in FIG. 4, the respective light surface 10 of the respective light conductor 20 is processed such that the entire light surface 10, as the light surface 10 formed from the individual light conductors 20 has in each case an adapted radius 24 such that a lighting unit 3 realized with a light surface 10 in the shape of a segment of a circle is formed. In a preferred design, the desired number of individual light conductors 20 is at the same time placed side by side between the closure plates, the entire light surface 10 then being produced with the desired radius 24. The radius 24 can be realized such that the lighting unit 3 does not engage in the path (labelling star).

A homogeneously illuminated light surface 10 is formed by this advantageous design. In order to be able to project the strip-shaped pattern 15 onto the container wall region 8, it is advantageously provided that the homogeneously illuminated light surface 10 is covered by a mask. The mask is not shown but can exhibit vertically extending slots of predeterminable widths and spacings. The mask can be formed by a diaphragm plate that is adapted to the radius 24.

Figure 6:
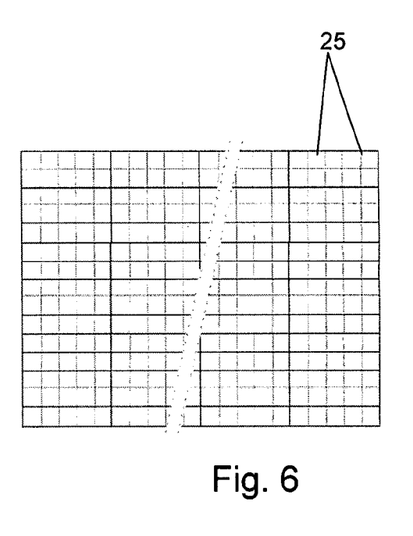
FIG. 6 shows a cascaded design of a plurality of lighting units in FIG. 4.

As can be seen in the diagram in FIG. 6 as an example, a plurality of lighting units 3 can be provided in a cascaded manner, it being possible for each lighting unit 3 to have a respective different mask on its light surface 10. The individual squares 25 shown small in FIG. 6 in this case each represent a light conductor 20. As represented as an example, a plurality of light conductors 20 can be arranged on top of one another and side by side.

LIST OF REFERENCES

1 Detecting system
2 Container/Bottle
3 Lighting unit
4 Optical arrangement
5 Camera
6 Light source
7 Light beams
8 Container wall region
9 Carrier element
10 Light surface
11 Rear side of 9
12 Conductor path
13 Photo strip
14 Vertical rows or lines
15 Vertical light pattern
16 Evaluation and control unit
17 Optical lens
18 End faces of 17
19 Embossing
20 Light conductor
21 Rear side of 20
22 Course of beam
23 Side faces of 20
24 Radius
25 Square

The invention claimed is:
1. An apparatus for assisting in positioning of a label on a container at a location relative to a feature formed at a selected location on a container wall of said container, said container wall having a circumference, said apparatus comprising a labelling machine and a detecting system, wherein the labelling machine comprises a labelling star that conveys a container past the detecting system, wherein said detecting system comprises a lighting unit having a plurality of light sources, the lighting unit being configured to project spaced-apart strip-shaped light beams onto a portion of a circumference of the container wall, wherein the portion of the circumference of the container wall is less than the entire circumference of the container wall, and an optical arrangement having at least one camera.

2. The apparatus of claim 1, wherein the lighting unit further comprises a carrier element having a light surface oriented towards the container, wherein a meaning of "carrier element" is an element that is a constituent part of said lighting unit, and that has a light surface that is oriented toward said container, and wherein a function of said carrier element is to have a light surface that is oriented toward said container.

3. The apparatus of claim 2, wherein on the light surface, the lighting unit comprises at least one conductor path on which light sources are located vertically arranged in spaced-apart vertically-aligned rows.

4. The apparatus of claim 2, wherein the light surface defines a sector of a circle.

5. The apparatus of claim 1, wherein the optical arrangement comprises a plurality of cameras.

6. The apparatus of claim 5, wherein at least one of the plurality of cameras has associated therewith an optical lens.

7. The apparatus of claim 2, wherein the lighting unit is formed by a plurality of light conductors located side-by-side, each having associated therewith a light source on a rear side thereof, and wherein the light surface defines a radius, wherein the light conductors are conductors that conduct light.

8. The apparatus of claim 2, wherein the lighting unit is formed by a plurality of light conductors located side-by-side, each having associated therewith a light source on a rear side thereof, and wherein the lighting unit further comprises a mask with vertically realized light outlet openings located on the light surface, wherein the light conductors are conductors that conduct light.

9. The apparatus of claim 8, wherein the mask comprises a diaphragm element that defines slot widths that can be predetermined and slot spacings that can be predetermined.

10. The apparatus of claim 7, wherein the light conductors comprise colorless, clear acrylic glass bars.

11. A method of using the apparatus recited in claim 1 for detecting a feature on a container, said method comprising: using a labelling star, bringing a container to detector, at the detector, using a plurality of light sources, projecting spaced-apart strips of light onto a container wall of said container; using an optical arrangement having at least one camera, observing a reflection of said project based in part on said observation, identifying a feature on said container wall.

12. The method of claim 11, further comprising labelling said container based at least in part on said identification of at least one feature on said container wall.

13. The apparatus of claim 10, wherein the plastic bars are developed as square bars and, in a planar manner, are located side-by-side by way of their respective adjacent side faces.

14. The method of claim 11, wherein said feature comprises a seam extending vertically along said container wall.

15. The method of claim 11, wherein said feature comprises an embossing on said container wall.

16. The method of claim 11, wherein said feature comprises a development feature on said container wall.

17. The apparatus of claim 5, wherein at least one of the cameras lacks an optical lens.

\* \* \* \* \*